US006034219A

United States Patent [19]
Hillman et al.

[11] Patent Number: 6,034,219
[45] Date of Patent: Mar. 7, 2000

[54] HUMAN MACROPHAGE ANTIGEN

[75] Inventors: Jennifer L. Hillman, San Jose; Janice Au-Young, Berkeley; Surya K. Goli, Sunnyvale, all of Calif.

[73] Assignee: Incyte Pharmaceuticals, Inc., Palo Alto, Calif.

[21] Appl. No.: 09/113,789

[22] Filed: Jul. 10, 1998

Related U.S. Application Data

[62] Division of application No. 08/690,095, Jul. 31, 1996, Pat. No. 5,792,648.

[51] Int. Cl.$^7$ ........................... C07K 14/47; C07K 16/18; A61K 38/00

[52] U.S. Cl. .................. 530/350; 530/387.1; 530/387.9; 514/2

[58] Field of Search ................................. 530/350, 387.1, 530/387.9; 514/2

[56] References Cited

FOREIGN PATENT DOCUMENTS 0 795 605 A1  9/1997  European Pat. Off. .
WO 95/27734  10/1995  WIPO .

OTHER PUBLICATIONS

Athamna, A., et al., "Lectinophagocytosis of Encapsulated *Klebsiella pneumoniae* Mediated by Surface Lectins of Guinea Pig Alveolar Macrophages and Human Monocyte–Derived Macrophages" *Infect. Immun.* 59:1673–1682 (1991).
Bronner, M.P., et al., "The bcl–2 Proto–Oncogene and the Gastrointestinal Epithelial Tumor Progression Model" *Amer. J. Path.*, 146:20–26 (1995).
Cerroni, L., et al., "bcl–2 Protein Expression in Cutaneous Malignant Melanoma and Benign Melanocytic Nevi" *Amer. J. Dermat.*, 17:7–11 (1995).
Chang, C., et al., "Molecular characterization of human CD94: a type II membrane glycoprotein related to the C–type lectin superfamily" *Eur. J. Immunol.*, 25:2433–2437 (1995).
Choi, S.S., et al., "A novel Bcl–2 related gene, Bfl–1, is overexpressed in stomach cancer and preferentially expressed in bone marrow" *Oncogene*, 11:1693–1698 (1995).
Craig, R.W., "The BCL–2 gene family" *Cancer Biology*, 6:35–43 (1995).
Erlacher, L., et al., "Differential Expression of the Protooncogene bcl–2 in Normal and Osteoarthritic Human Articular Cartilage" *J. Rheum.*, 22:926–31 (1995).
Garatti, S.A., et al., "bcl–1, bcl–2, p53, c–myc, and lyt–10 Analysis in Cutaneous Lymphomas" *Cancer Res.*, 139:249–261 (1995).
Goswami, S., et al., "Mycotin: a lectin involved in the adherence of Mycobacteria to macrophages" *FEBS Lett.*, 355:183–186 (1994).
Houchins, J.P., et al., "DNA Sequence Analysis of NKG2, a Family of Related cDNA Clones Encoding Type II Integral Membrane Proteins on Human Natural Killer Cells" *J. Exp. Med.*, 173:1017–1020 (1991).
Kroll, J.S., et al., "Copper–Zinc Superoxide Dismutase of *Haemophilus influenzae* and *H. Parainfluenzae*" *J. Bacter.*, 173:7449–7457 (1991).
Lin, E.Y., et al., "Characterization of A1, a Novel Hemopoietic–Specific Early–Response Gene with Sequence Similarity to bcl–2$^1$" *J. Immunol.*, 151:1979–1988 (1993).
Linnik, M.D., et al., "Expression of bcl–2 From a Defective Herpes Simplex Virus–1 Vector Limits Neuronal Death in Focal Cerebral Ischemia" *Stroke*, 26:1670–1675 (1995).
Minn, A.J., "Expression of Bcl–$x_L$ Can Confer a Multidrug Resistance Phenotype" *Blood*, 86:1903–1910 (1995).
Newcomb, E.W., "P53 Gene Mutations in Lymphoid Diseases and Their Possible Relevance to Drug Resistance" *Leuk. and Lymph.*, 17:211–221 (1995).
Oda, S., et al., "Binding of Activated Macrophages to Tumor Cells through a Macrophage Lectin and Its Role in Macrophage Tumoricidal Activity" *J. Biochem.*, 105:1040–1043 (1989).
Russell, M.E., et al., "Identification and Upregulation of Galactose/N–acetylgalactosamine Macrophage Lectin in Rat Cardiac Allografts with Arteriosclerosis" *J. Clin. Invest.*, 94:722–730 (1994).
Shimizu, S., et al., "Prevention of hypoxia–induced cell death by Bcl–2 and Bcl–xL" *Nature*, 374:811–816 (1995).
Silvestris, F., et al., "Apoptosi, o morte cellulare programmata: meccanismi regolartori e fisiopatologia" *Ann. Ital. Med. Int.*, 10:7–13 (1995).
Spiess, M., "The Asialoglycoprotein Receptor: A Model of Endocytic Transport Receptors," *Biochem.* 29:10009–10018 (1990).
Suzuki, N., et al., "Molecular Cloning and Expression of cDNA Encoding Human Macrophage C–Type Lectin" *J. Immunol.* 156:128–135 (1996).
Teixeira, C., et al., "Estrogen Promotes Chemotherapeutic Drug Resistance by a Mechanism Involving Bcl–2 Proto–Oncogene Expression in Human Breast Cancer Cells" *Cancer Res.*, 55:3902–3907 (1995).
Tsujimoto, Y., et al., "Analysis of the structure, transcripts, and protein products of bcl–2, the gene involved in human follicular lymphoma" *Proc. Natl. Acad. Sci.*, 83:5214–5218 (1986).
Zimmerman, K., et al., "Heterogenic mRNAs with an Identical Protein–coding Region of the Human Embryonic Myosin Alkali Light Chain in Skeletal Muscle Cells" *J. Mol. Biol.*, 211:505–513 (1990).

*Primary Examiner*—Nancy A Johnson
*Attorney, Agent, or Firm*—Incyte Pharmaceuticals, Inc.

[57] ABSTRACT

The present invention provides a polynucleotide which identifies and encodes a novel human macrophage antigen (TMAH). The invention provides for genetically engineered expression vectors and host cells comprising the nucleic acid sequence encoding TMAH. The invention also provides for the use of substantially purified TMAH and its agonists, antibodies, antagonists or inhibitors in pharmaceutical compositions for treatment of diseases associated with expression of TMAH. The invention also describes diagnostic assays which utilize the polynucleotide to hybridize with the genomic sequence or transcripts encoding TMAH and anti-TMAH antibodies which specifically bind to TMAH.

5 Claims, 8 Drawing Sheets

```
                                                           45              54
                        18           27           36
5' GAA GTG TAA ACT TGT AAG CTT CCG TTT ATA AAC AGA AGT TTA AAA TTA
   9

99              108
                        72           81           90
   TAG GTC NCT GTT TAA CAT TCA GCT CTG TTA ACT CAC TCA TCT TTT TGT GTT TTT
   63

153             162
                       126          135          144
   ACA CTT TGT CAA GAT TTC TTT ACA TAT TCA TCA ATG TCT GAA GAA GTT ACT TAT
   117                                            M   S   E   E   V   T   Y 207             216
                       180          189          198
   GCA GAT CTT CAA TTC CAG AAC TCC AGT GAG ATG GAA AAA ATC CCA GAA ATT GGC
   171  A   D   L   Q   F   Q   N   S   S   E   M   E   K   I   P   E   I   G 261             270
                       234          243          252
   AAA TTT GGG GAA AAA GCA CCT CCA CCC TCT CAT GTA TGG CGT CCA GCA GCC
   225  K   F   G   E   K   A   P   P   P   S   H   V   W   R   P   A   A 315             324
                       288          297          306
   TTG TTT CTG ACT CTT CTG TGC CTT CTG TTG CTC ATT GGA TTG GGA GTC TTG GCA
   279  L   F   L   T   L   L   C   L   L   L   L   I   G   L   G   V   L   A 369             378
                       342          351          360
   AGC ATG TTT CAT GTA ACT TTG AAG ATA GAA ATG AAA AAA AAC AAA CTA CAA
   333  S   M   F   H   V   T   L   K   I   E   M   K   K   N   K   L   Q
```

FIGURE 1A

```
AAC ATC AGT GAA GAG CTC CAG AGA AAT ATT TCT CTA CAA CTG ATG AGT AAC ATG
 N   I   S   E   E   L   Q   R   N   I   S   L   Q   L   M   S   N   M
387         396         405         414         423         432

AAT ATC TCC AAC AAG ATC AGG AAC CTC TCC ACC ACA CTG CAA ATA GCC ACC
 N   I   S   N   K   I   R   N   L   S   T   T   L   Q   I   A   T
441         450         459         468         477         486

AAA TTA TGT CGT GAG CTA TAT AGC AAA GAA CAA GAG CAC AAA TGT AAG CCT TGT
 K   L   C   R   E   L   Y   S   K   E   Q   E   H   K   C   K   P   C
495         504         513         522         531         540

CCA AGG AGA TGG ATT TGG CAT AAG GAC AGC TGT TAT TTC CTA AGT GAT GAT GTC
 P   R   R   W   I   W   H   K   D   S   C   Y   F   L   S   D   D   V
549         558         567         576         585         594

CAA ACA TGG CAG GAG AGT AAA ATG GCC TGT GCT CAG AAT GCC AGC CTG TTG
 Q   T   W   Q   E   S   K   M   A   C   A   Q   N   A   S   L   L
603         612         621         630         639         648

AAG ATA AAC AAC AAA AAT GCA TTG GAA TTT ATA AAA TCC CAG AGT AGA TCA TAT
 K   I   N   N   K   N   A   L   E   F   I   K   S   Q   S   R   S   Y
657         666         675         684         693         702

GAC TAT TGG CTG GGA TTA TCT CCT GAA GAA GAT TCC ACT CGT GGT ATG AGA GTG
 D   Y   W   L   G   L   S   P   E   E   D   S   T   R   G   M   R   V
711         720         729         738         747         756
```

FIGURE 1B

```
      765             774             783             792             801             810
GAT AAT ATA ATC AAC TCC TCT GCC TGG GTT ATA AGA AAC GCA CCT GAC TTA AAT
 D   N   I   I   N   S   S   A   W   V   I   R   N   A   P   D   L   N 819             828             837             846             855             864
AAC ATG TAT TGT GGA TAT ATA AAT AGA CTA TAT GTT CAA TAT TAT CAC TGC ACT
 N   M   Y   C   G   Y   I   N   R   L   Y   V   Q   Y   Y   H   C   T 873             882             891             900             909             918
TAT AAA AGA ATG ATA TGT GAG AAG ATG GCC AAT CCA GTG CAG TTG GTT CTA
 Y   K   R   M   I   C   E   K   M   A   N   P   V   Q   L   V   L 927             936             945             954             963
CAT ATT TTA GGG AGG CAT GAG GCA TCA ATC AAA TAC ATT TAA GGA GTG TAG GG 3'
 H   I   L   G   R   H   E   A   S   I   K   Y   I
```

HUMAN MACROPHAGE ANTIGEN

This application is a divisional application of U.S. application Ser. No. 08/690,095, filed Jul. 31, 1996 now U.S. Pat. No. 5,792,648.

FIELD OF THE INVENTION

The present invention relates to nucleic acid and amino acid sequences of a novel human macrophage antigen which shares the features characterizing hemopoietic-specific early response proteins and calcium dependent lectins and to the use of these sequences in the diagnosis, study, prevention and treatment of disease.

BACKGROUND OF THE INVENTION

The mouse hemopoietic-specific early response protein, A1, has been studied by Lin et al (1993; J Immunol 151:1979–88) who first reported on its relationship to Bcl-2 (B-cell leukemia/lymphoma 2)and Mcl-1. A1 belongs to a gene family that has been characterized in humans, mice and chickens (Craig RW (1995) Semin Cancer Biol 6:35–43) and includes Bfl-1, Bcl-2, Bcl-x, Bcl-xL, bax, and mcl-1. These genes regulate cell viability; in some cases, preventing toxicity to antibiotics and anticancer drugs (Minn A J et al (1995) Blood 86:1903–1910), and in others, governing the apoptosis necessary for tissue differentiation and organismal development. The exact mechanism by which A1, Bcl-2 and related genes promote cell survival is not known; however, they may function through the inhibition of cysteine proteases.

The coding region of the murine A1 (Lin et al, supra) consists of 648 nucleotides which encode 216 amino acids. The open reading frame ($T_{474}$) and the 3' untranslated region ($T_{715}$) each contain a TACAAA motif which is found in many immediate early genes and may be essential for induction. The deduced protein has a predicted molecular weight of 20,024, an isoelectric point of 5.05, and a potential glycosylation site at $N_{128}$. The absence of a secretion signal led Lin et al (supra) to suggest that A1 might be an intracellular rather than a secreted protein.

Expression of A1 has been detected in bone marrow, spleen and thymus and is induced by GM-CSF (granulocyte-macrophage colony stimulating factor) in several hematopoietic cell lineages, including T-helper lymphocytes, macrophages and neutrophils, and in myeloid cell lines induced to differentiate by IL-3. A1 is induced in a macrophage tumor cell line by lipopolysaccharide. The protein synthesis inhibitor cycloheximide works as an agonist to induce the long-term expression of A1, a feature previously reported for other early response genes (Lin, supra). Neither serum nor the cytokines, interleukin (IL)-1 alpha or IL-6, induce A1 expression.

Calcium dependent or C-type lectin receptors are widely expressed in cells of the immune system. Their characteristic features include: 1) a cytosolic amino terminus containing at least one potential tyrosine phosphorylation site which may be involved in signal transduction and several prolines which may prevent steric interference between the cytosolic and membrane spanning domains, 2) a short, approximately 20, hydrophobic amino acid transmembrane domain, and 3) a series of cysteine residues which appear to function as an extracellular carbohydrate recognition domain (Speiss M (1990) Biochem 29:10009–18). When the extracellular carbohydrate binding domain is separated from the membrane spanning domain by protease activity, it maintains both its structural and functional integrity. As described below, macrophage C-type lectin receptors perform a variety of functions in the recognition and destruction of foreign cells.

Diseases or Activities Associated with A1 or C-lectin Family Genes

Alterations or aberrations in A1 family gene expression are known to result in premature cell death or in cancer. The best known gene in this family, Bcl-2, is a proto-oncogene associated with human follicular lymphoma (Tsujimoto Y and Croce CM (1986) Proc Nat Acad Sci 83:5214), malignant melanomas, and solid tumors such as carcinomas of the lung, prostate and nasopharynx (Cerroni L (1995) Am J Dermatopathol 17:7–11). In patients with AIDS, there is also a high correlation between Epstein-Barr virus (EBV) and primary brain lymphomas. The virus's latent membrane protein 1 has been reported to transactivate the Bcl-2 gene and in one study, both genes were expressed in 10 out of 11 cases of AIDS-related primary brain lymphoma. Expression of Bcl-2 is far less common in systemic lymphomas and cutaneous B or T cell lymphomas (Garatti S A et al (1995) Recent Results Cancer Res 139:249–261).

Estrogen also increases Bcl-2 expression promoting chemotherapeutic drug resistance in an estrogen-responsive human breast cancer cell line (Teizeira C et al (1995) Cancer Res 55: 3902–3907). Bcl-2 is normally expressed in the epithelial regenerative compartment or the basal crypts of the colon and small intestine. Overexpression of Bcl-2 was not seen in inflammatory gastrointestinal conditions such as ulcerative colitis, Crohn's disease, or hamartomatous polyps; but it was common in hyperplastic colonic polyps and in the majority of dysplastic lesions, adenomas and adenocarcinomas. The presence of excess Bcl-2 in tissue surrounding the lesions suggests that the neoplasias arose from tissue in which earlier conversion to abnormal Bcl-2 expression occurred (Bronner M P et al (1995) Am J Pathol 146: 20–26).

Some of the other A1 family genes are now being characterized. Clinical studies on the gene, Bfl-1 (Choi S S et al (1995) Oncogene 11: 1693–98) isolated from human fetal liver and highly expressed in bone marrow have shown a correlation between expression of Bfl-1 and stomach cancer. The studies suggest that Bfl-1 may promote the survival of stomach cancer cells by preventing apoptosis. Expression of Bcl-XL dramatically reduces cytotoxicity to antibiotics and chemotherapeutics such as bleomycin, cysplatin, hygromycin, and vincristine, (Minn, supra; Newcomb E W (1995) Leuk Lymphoma 17: 211–221).

Silvestris F et al (1995; Ann Ital Med Int 10: 7–13) showed that A1 family genes are involved in autoimmune conditions such as lupus erythematosus and degenerative neuropathies such as Alzheimer's disease; and Erlacher et al (1995; J Rheumatol 22: 926–931) reported on the increased expression of Bcl-2 in chondrocytes adjacent to osteoarthritic defects. Other studies suggest that inducing the expression of A1 family genes may serve to rescue neurons from programmed cell death due to hypoxia (Shimizu et al (1995) Nature 374:811–816) or cerebral ischemic stroke (Linnik M D et al (1995; Stroke 26:1670–74).

Unique C type lectin receptors may direct the macrophages to abnormal or diseased cells where they specifically interact with surface antigens. For example, *Klebsiella pneumoniae* serotypes displaying certain surface mannose polysaccharide sequences bind to and are subsequently internalized and destroyed by macrophages (Athamna A et al (1991) Infect Immun 59: 1673–1682). Similarly, the Tn Ag of a well-known human carcinoma-associated epitope (Suzki N et al (1996) J Immunol 156: 128–135) is recognized by a human macrophage C-type lectin. Binding of macrophages to mastocytoma cells occurs through the Gal/GalNAc-specific macrophage lectin and activates the tumor cell killing mechanism (Oda S et al (1989) J Biochem 105: 1040–1043).

Some diseases are due to defects in the recognition of what is foreign as mediated via the macrophage lectin receptor, and some conditions such as graft and transplant rejection and pathogen colonization of host macrophages derive from normal, yet undesirable, functioning of macrophages. For example, in rat cardiac allografts, expression of macrophage cell-surface lectins were linked to chronic rejection. In this case the lectin served as a possible mediator of macrophage infiltration (Russel M E et al (1994) J Clin Invest 94: 722–730). Also, the attachment of such pathogens as *Mycobacteria tuberculosis* via mannose-specific lectin receptors expressed on the macrophages (Goswami S et al (1994) FEBS Lett 355: 183–186) is the preliminary step in pathogenesis.

Macrophage antigens/lectins clearly play an important role in the recognition and destruction of foreign and diseased cells. The selective modulation of the expression and specificity of a novel human macrophage antigen may allow the successful management of diseases related to macrophage function, allowing natural cytolysis via specific targeting to infected host cells or tumors or preventing graft rejection and pathogen colonization.

SUMMARY

The present invention discloses a novel human macrophage antigen, hereinafter referred to as TMAH and characterized as having structural homology to both-mammalian A1 and the C-type lectins. Accordingly, the invention features a substantially purified TMAH, as shown in the amino acid sequence of SEQ ID NO:1. This sequence has a distinctive $A_{42}$–$A_{61}$ transmembrane motif and an extracellular domain, from residue $S_{62}$ to residue $I_{272}$, which appears to bind to molecules such as lectins, carbohydrates or glycoproteins.

One aspect of the invention features isolated and substantially purified polynucleotides which encode TMAH. In a particular aspect, the polynucleotide is the nucleotide sequence of SEQ ID NO:2. In addition, the invention features polynucleotide sequences that hybridize under stringent conditions to SEQ ID NO:2.

The invention further relates to the nucleic acid sequence encoding TMAH, oligonucleotides, peptide nucleic acids (PNA), fragments, portions or antisense molecules thereof. The invention also provides for the use of antisense molecules to disrupt the expression of the genomic sequence encoding TMAH particularly in tissues involved in the development of lymphomas or carcinomas. The present invention relates, in part, to the inclusion of the nucleic acid sequence encoding TMAH in an expression vector which can be used to transform host cells or organisms.

The present invention also relates to a method for producing TMAH or a fragment thereof, antibodies which bind specifically to TMAH, and a pharmaceutical composition comprising a substantially purified fragment of TMAH in conjunction with a suitable pharmaceutical carrier.

BRIEF DESCRIPTION OF THE FIGURES

FIGS. 1A and 1B show the amino acid sequence (SEQ ID NO:1) and nucleic acid sequence (SEQ ID NO:2) of the human macrophage antigen produced using MacDNAsis™ software (Hitachi Software Engineering Co Ltd).

FIG. 2 shows the amino acid sequence alignments among human macrophage antigen (SEQ ID NO:1), mouse A1 (GI 239274; SEQ ID NO:3), human bcl-2 α (GI 179367; SEQ ID NO:4), and human mcl-1 (GI 34678; SEQ ID NO: 5) produced using the multisequence alignment program of DNAStar™ software (DNAStar Inc, Madison Wis.

FIG. 3 shows the amino acid sequence alignments among human macrophage antigen (SEQ ID NO:1), Type II integral membrane proteins (GI 35061, SEQ ID NO:6; GI 35059, SEQ ID NO:7; and GI35057, SEQ ID NO:8) and CD94 (GI 1098617, SEQ ID NO:9).

DESCRIPTION OF THE INVENTION

Definitions

Definitions

Figure 4:
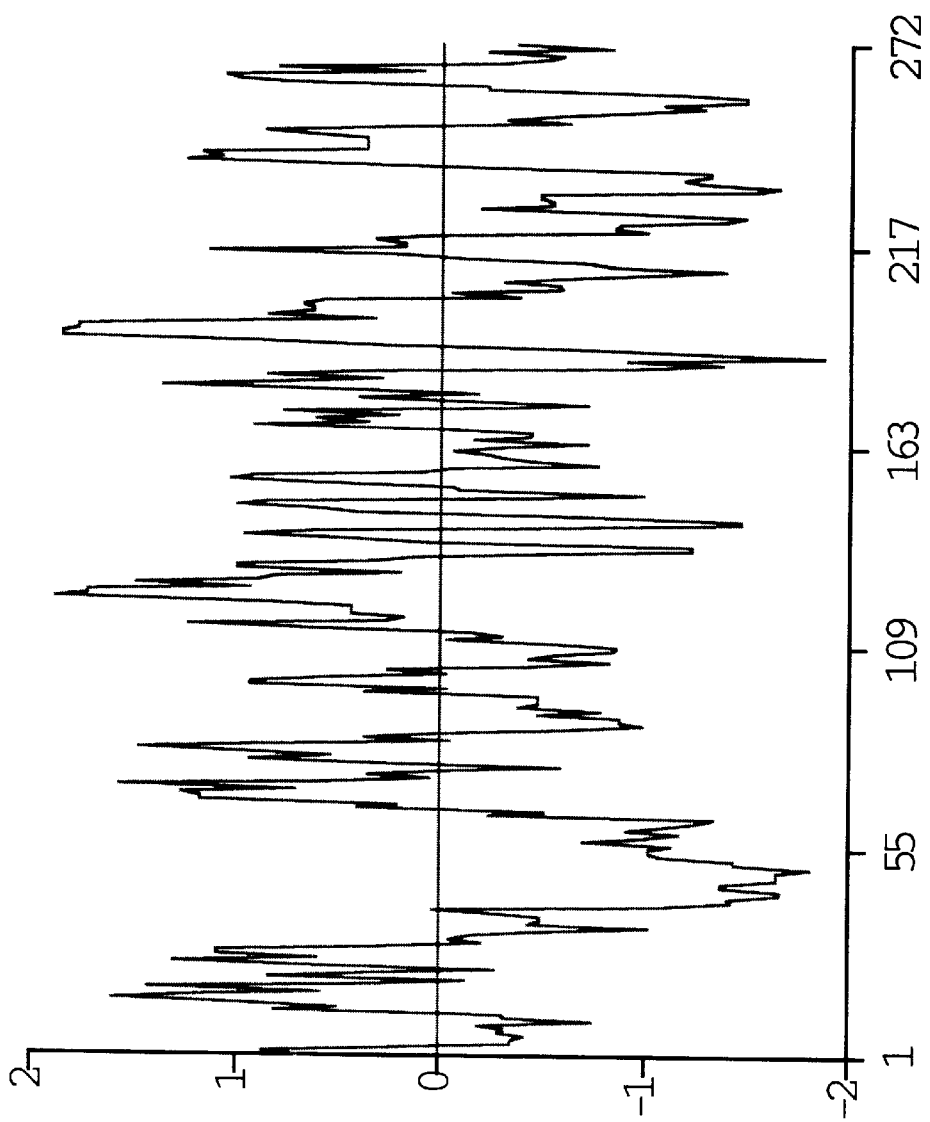
FIG. 4 shows the hydrophobicity plot for human macrophage antigen, SEQ ID NO:1, generated using MacDNAsis software; the X axis reflects amino acid position, and the negative Y axis, hydrophobicity.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring LRRP.

A "substitution" results from the replacement of one or more nucleotides or amino acids by different nucleotides or amino acids, respectively.

As used herein, LRRP refers to the amino acid sequence of substantially purified LRRP obtained from any species, particularly mammalian, including bovine, ovine, porcine, murine, equine, and preferably human, from any source whether natural, synthetic, semi-synthetic or recombinant.

A "variant" of LRRP is defined as an amino acid sequence that is different by one or more amino acid substitutions. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

The term "biologically active" refers to a LRRP having structural, regulatory or biochemical functions of a naturally occurring LRRP. Likewise, "immunologically-active" defines the capability of the natural, recombinant or synthetic LRRP, or any oligopeptide thereof, to induce a specific immune response in appropriate animals or cells and to bind with specific antibodies.

The term "derivative" as used herein refers to the chemical modification of a nucleic acid encoding LRRP or the encoded LRRP. Illustrative of such modifications would be replacement of hydrogen by an alkyl, acyl, or amino group. A nucleic acid derivative would encode a polypeptide which retains essential biological characteristics of natural LRRP.

As used herein, the term "substantially purified" refers to molecules, either nucleic or amino acid sequences, that are removed from their natural environment, isolated or separated, and are at least 60% fRee, preferably 75% free, and most preferably 90% free from other components with which they are naturally associated.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification is defined as the production of additional copies of a nucleic acid sequence and is generally carried out using polymerase chain reaction technologies well known in the art (Dieffenbach C W and G S Dveksler (1995) *PCR Primer, a Laboratory Manual,* Cold Spring Harbor Press, Plainview N.Y.).

"Stringency" typically occurs in a range from about Tm–5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

Description

The present invention relates to a novel human macrophage antigen initially identified as Incyte Clone 513418 (SEQ ID NO:2), using a computer-generated search for amino acid sequence alignments. The invention also relates to the use of the disclosed nucleic acid and amino acid sequences in the study, diagnosis, prevention and treatment of diseases associated with expression of these sequences. Although the human macrophage antigen encoding nucleotide sequence was identified among the partial cDNAs from a macrophage library (MPHGNOT03), the naturally occurring expression is not necessarily limited to macrophages.

The present invention also encompasses human macrophage antigen variants. A preferred variant is one having at least 80% amino acid sequence similarity to the TMAH of SEQ ID NO:1, a more preferred variant is one having at least 90% sequence similarity to SEQ ID NO:1, and a most preferred variant is one having at least 95% sequence similarity to SEQ ID NO:1.

Figure 2A:
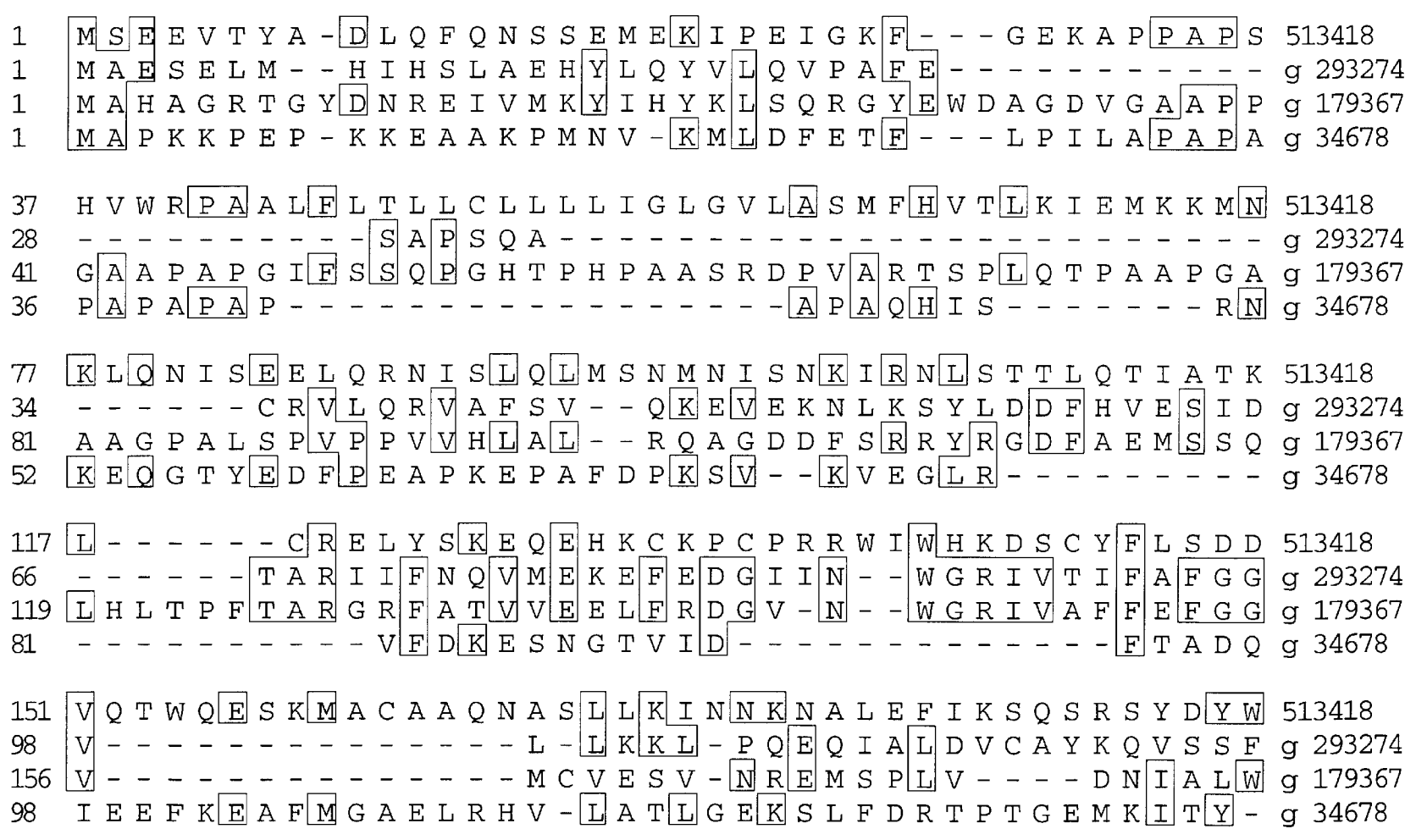
Figure 2B:
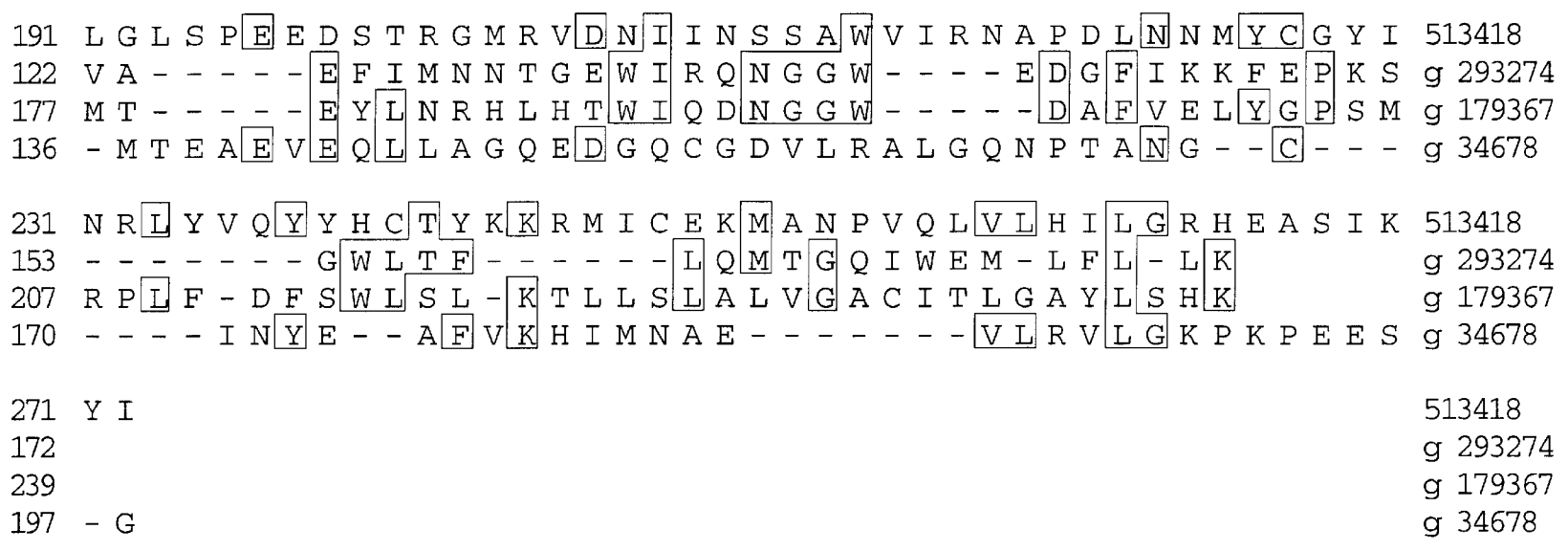
Figure 3A:
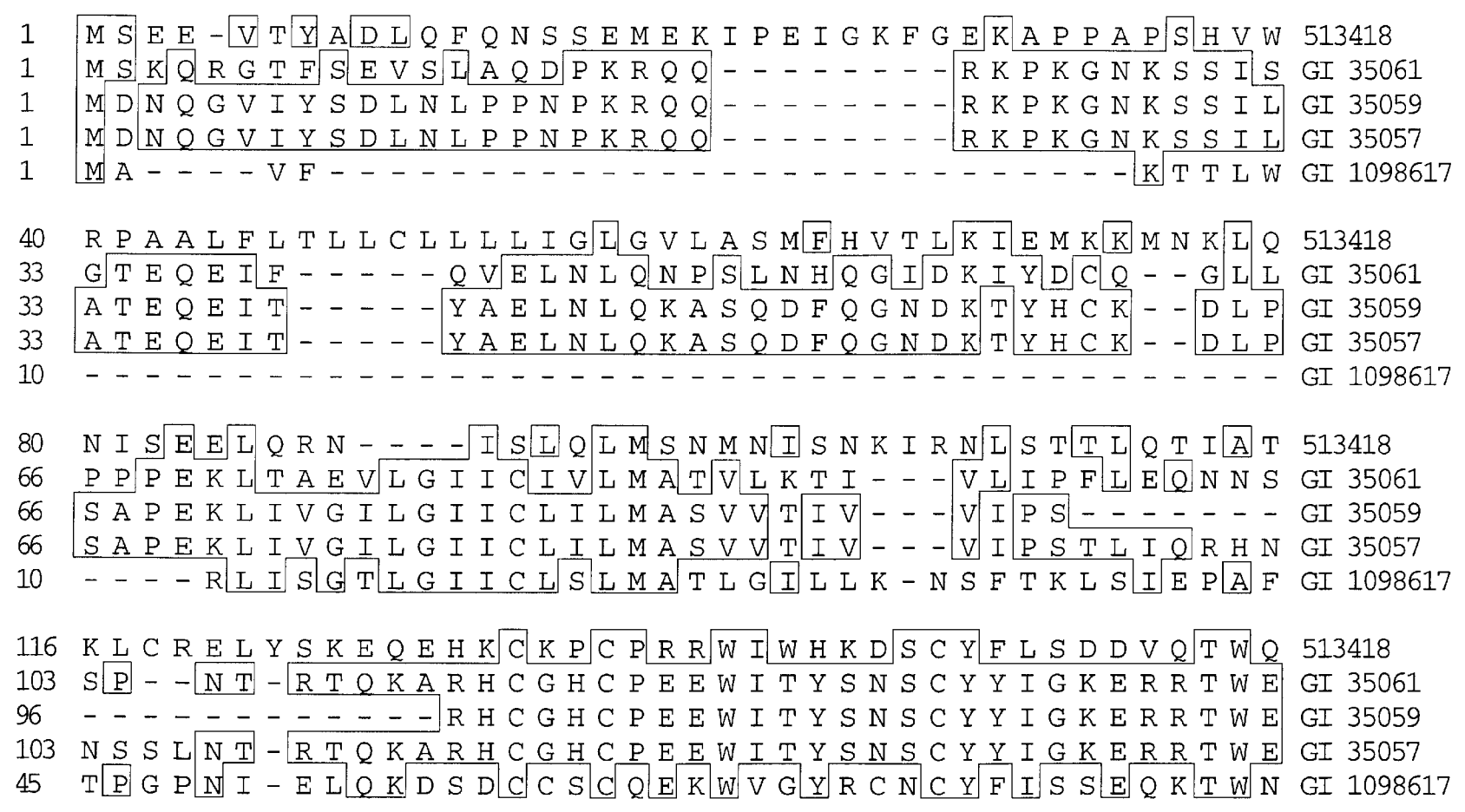
Figure 3B:
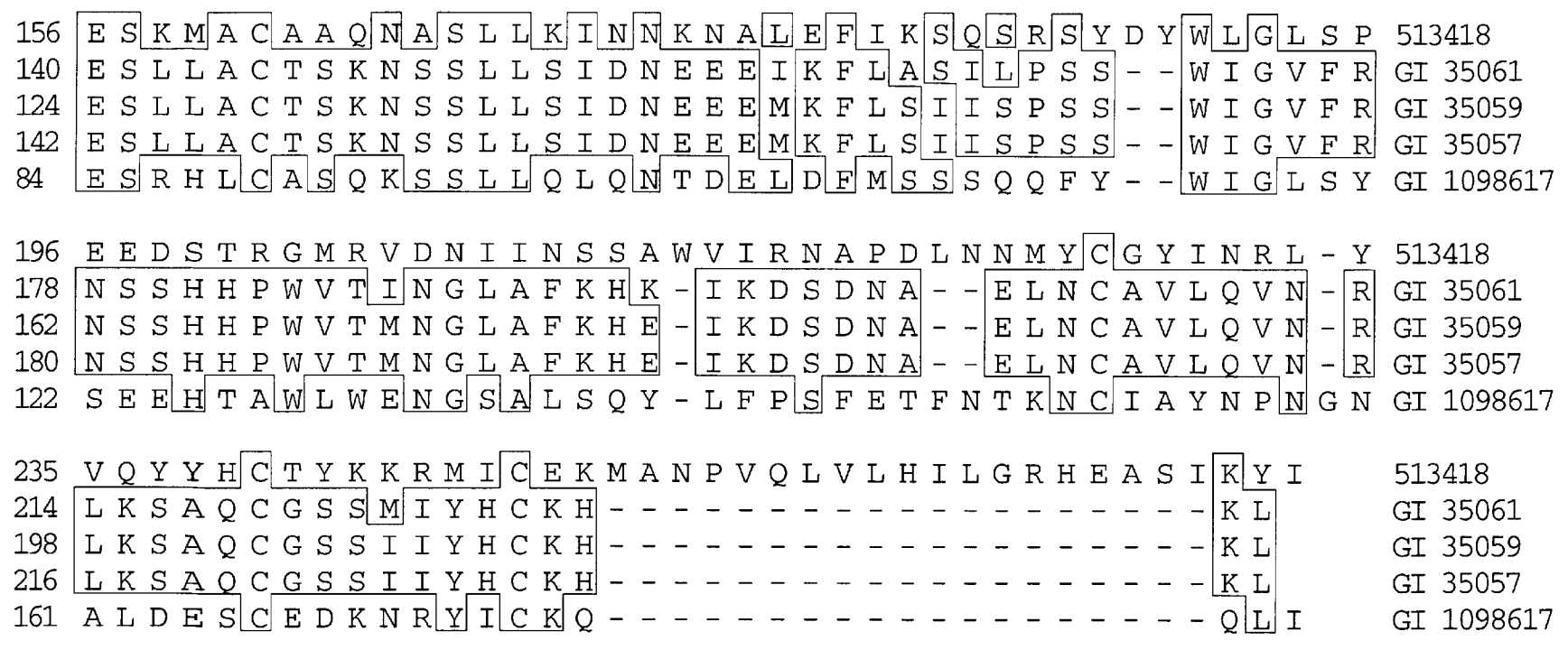

The nucleic acid sequence, SEQ ID NO:2; disclosed herein encodes the amino acid sequence, SEQ ID NO:1, for the novel human macrophage antigen, designated he rein as TMAH. The present invention is based, in part, on the amino acid homology among TMAH, mouse A1 (GI 239274;), human bcl-2 α (GI 179367;), and human mcl-1 (GI 34678;) as shown in FIG. 2, and among TMAH, the Type II integral membrane proteins (GI 35061, SEQ ID NO:6; GI 35059, SEQ ID NO:7; and GI35057, SEQ ID NO:8) and CD94 (GI 1098617, SEQ ID NO:9) as shown in FIG. 3. TMAH has 20% amino acid sequence identity to each of these groups and is a transmembrane protein with an isoelectric point of 8.79. The homology which TMAH shares with the other A1 family members is spread over the length of the amino acid sequence and includes conserved residues at $F_{27}$, $P_{35}$, $R_{119}$, $W_{139}$, $F_{146}$, and $W_{214}$ (FIG. 2). In addition, 23 serine and nine tyrosine residues are located in either the cytoplasmic or the extracellular portion of TMAH and present potential sites for phosphorylation. The transmembrane spanning residues of TMAH, from $R_{40}$ to $A_{61}$ inclusive, closely matches that of CD94 (Chang C et al (1995) Eur J Immunol 25: 2433–2437). The extracellular carbohydrate binding domain of TMAH contains the disulfide forming residues $C_{130}$, $C_{133}$, $C_{144}$, $C_{161}$, $C_{227}$, $C_{240}$ and $C_{248}$ (FIG. 3). TMAH is 272 amino acids long, has a potential cytoplasmic phosphorylation site at $Y_7$, and has seven potential glycosylation sites, $N_{14}$, $N_{80}$, $N_{88}$, $N_{98}$, $N_{105}$, $N_{165}$, and $N_{210}$ (FIG. 2).

The TMAH Coding Sequences

The nucleic acid and deduced amino acid sequences of TMAH are shown in FIGS. 1A and 1B. In accordance with the invention, any nucleic acid sequence which encodes TMAH can be used to generate recombinant molecules which express TMAH. In a specific embodiment described herein, a partial sequence encoding TMAH was first isolated as Incyte Clone 513418 from a macrophage cDNA library (MPHGNOT03).

It will be appreciated by those skilled in the art that as a result of the degeneracy of the genetic code, a multitude of TMAH-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence encoding naturally occurring TMAH, and all such variations are to be considered as being specifically disclosed.

Although nucleotide sequences which encode TMAH and its variants are preferably capable of hybridizing to the nucleotide sequence of the naturally occurring sequence under appropriately selected conditions of stringency, it may be advantageous to produce nucleotide sequences encoding TMAH or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding TMAH and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding TMAH and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a sequence encoding TMAH or any portion thereof.

Also included within the scope of the present invention are polynucleotide sequences that are capable of hybridizing to the nucleotide sequence of FIGS. 1A and 1B under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology,* Vol 152, Academic Press, San Diego Calif.) incorporated herein by reference, and may be used at a defined "stringency".

Altered nucleic acid sequences encoding TMAH which may be used in accordance with the invention include deletions, insertions or substitutions of different nucleotides resulting in a polynucleotide that encodes the same or a functionally equivalent TMAH. The protein may also show deletions, insertions or substitutions of amino acid residues which produce a silent change and result in a functionally equivalent TMAH. Deliberate amino acid substitutions may be made on the basis of similarity in polarity, charge, solubility, hydrophobicity, hydrophilicity, and/or the amphipathic nature of the residues as long as the biological activity of TMAH is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles encoding TMAH. As used herein, an "allele" or "allelic sequence" is an alternative form of the nucleic acid sequence encoding TMAH. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, Sequenase® (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

Extending the Polynucleotide Sequence

The polynucleotide sequence encoding TMAH may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about $_{68°–72}$° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequence is walking PCR (Parker J D et al (1991) Nucleic Acids Res 19:3055–60), a method for targeted gene walking. Alternatively, PCR, nested primers, PromoterFinder™ (Clontech, Palo Alto Calif.) and PromoterFinder libraries can be used to walk in genomic DNA. This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze either the size or confirm the nucleotide sequence in sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide Sequence

In accordance with the present invention, polynucleotide sequences which encode TMAH, fragments of the polypeptide, fusion proteins or functional equivalents thereof may be used in recombinant DNA molecules that direct the expression of TMAH in appropriate host cells. Due to the inherent degeneracy of the genetic code, other DNA sequences which encode substantially the same or a functionally equivalent amino acid sequence, may be used to clone and express TMAH. As will be understood by those of skill in the art, it may be advantageous to produce TMAH-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of TMAH expression or to produce recombinant RNA transcripts having desirable properties, such as a longer half-life, than transcripts produced from naturally occurring sequence.

The nucleotide sequences of the present invention can be engineered in order to alter a TMAH-encoding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant TMAH-encoding sequence may be ligated to a heterologous sequence to encode a fusion protein. For example, for screening of peptide libraries for inhibitors of TMAH activity, it may be useful to encode a chimeric TMAH protein that is recognized by a commercially available antibody. A fusion protein may also be engineered to contain a cleavage site located between a TMAH and the heterologous protein sequence, so that the TMAH may be cleaved and substantially purified away from the heterologous moiety.

In an alternate embodiment of the invention, the sequence encoding TMAH may be synthesized, whole or in part, using chemical methods well known in the art (see Caruthers M H et al (1980) Nuc Acids Res Symp Ser 215–23, Horn T et al(1980) Nuc Acids Res Symp Ser 225–32, etc). Alternatively, the protein itself could be produced using chemical methods to synthesize a TMAH amino acid sequence, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg, Creighton (1983) *Proteins, Structures and Molecular Principles*, WH Freeman and Co, New York N.Y.). The composition of the synthetic peptides may be confirmed by amino acid analysis or sequencing (eg, the Edman degradation procedure; Creighton, supra). Additionally the amino acid sequence of TMAH, or any part thereof, may be altered during direct synthesis and/or combined using chemical methods with sequences from other proteins, or any part thereof, to produce a variant polypeptide.

Expression Systems

In order to express a biologically active TMAH, the nucleotide sequence encoding TMAH or its functional equivalent, is inserted into an appropriate expression vector, ie, a vector which contains the necessary elements for the transcription and translation of the inserted coding sequence.

Methods which are well known to those skilled in the art can be used to construct expression vectors containing a TMAH-encoding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual,* Cold Spring Harbor Press, Plainview N.Y. and Ausubel F M et al (1989) *Current Protocols in Molecular Biology,* John Wiley & Sons, New York N.Y.

A variety of expression vector/host systems may be utilized to contain and express a TMAH-encoding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription-and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla Calif.) or pSport1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of the sequence encoding TMAH, vectors based on SV40 or EBV may be used with an appropriate selectable marker.

In bacterial systems, a number of expression vectors may be selected depending upon the use intended for TMAH. For example, when large quantities of TMAH are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the sequence encoding TMAH may be ligated into the vector in frame with sequences for the amino-terminal Met and the subsequent 7 residues of $\beta$-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding TMAH may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Hill *Yearbook of Science and Technology* (1992) McGraw Hill New York N.Y., pp 191–196 or Weissbach and Weissbach (1988) *Methods for Plant Molecular Biology,* Academic Press, New York N.Y., pp 421–463.

An alternative expression system which could be used to express TMAH is an insect system. In one such system, *Autographa californica* nuclear polyhedrosis virus (AcNPV) is used as a vector to express foreign genes in *Spodoptera frugiperda* cells or in Trichoplusia larvae. The sequence encoding TMAH may be cloned into a nonessential region of the virus, such as the polyhedrin gene, and placed under control of the polyhedrin promoter. Successful insertion of the sequence encoding TMAH will render the polyhedrin gene inactive and produce recombinant virus lacking coat protein coat. The recombinant viruses are then used to infect *S. frugiperda* cells or Trichoplusia larvae in which TMAH is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, a sequence encoding TMAH may be ligated into an adenovirus transcription/translation complex consisting of the late promoter and tripartite leader sequence. Insertion in a nonessential E1 or E3 region of the viral genome will result in a viable virus capable of expressing in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a sequence encoding TMAH. These signals include the ATG initiation codon and adjacent sequences. In cases where the sequence encoding TMAH, its initiation codon and upstream sequences are inserted into the most appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express TMAH may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt-cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the sequence encoding TMAH is inserted within a marker gene sequence, recombinant cells containing the sequence encoding TMAH can be identified by the absence of marker gene function. Alternatively, a marker gene can be placed in tandem with the sequence encoding TMAH under the control of a single promoter. Expression of the marker gene in response to induction or selection usually indicates expression of the tandem sequence as well.

Alternatively, host cells which contain the coding sequence for TMAH and express TMAH may be identified by a variety of procedures known to those of skill in the art. These procedures include, but are not limited to, DNA— DNA or DNA-RNA hybridization and protein bioassay or immunoassay techniques which include membrane, solution, or chip based technologies for the detection and/or quantification of the nucleic acid or protein.

The presence of the polynucleotide sequence encoding TMAH can be detected by DNA—DNA or DNA-RNA hybridization or amplification using probes, portions or fragments of the sequence encoding TMAH. Nucleic acid amplification based assays involve the use of oligonucleotides or oligomers based on the nucleic acid sequence to detect transformants containing DNA or RNA encoding TMAH. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of TMAH, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on TMAH is preferred, but a competitive binding assay may be employed. These and other assays are described, among other places, in Hampton R et al (1990, *Serological Methods, a Laboratory Manual*, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting related sequences include oligolabeling, nick translation, end-labeling or PCR amplification using a labeled nucleotide. Alternatively, the TMAH-encoding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of TMAH

Host cells transformed with a nucleotide sequence encoding TMAH may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing TMAH-encoding sequence can be designed with signal sequences which direct secretion of TMAH through a prokaryotic or eukaryotic cell membrane. Other recombinant constructions may join the sequence encoding TMAH to nucleotide sequence encoding a polypeptide domain which will facilitate purification of soluble proteins (Kroll D J et al (1993) DNA Cell Biol 12:441–53; cf discussion of vectors infra containing fusion proteins).

TMAH may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and TMAH is useful to facilitate purification. One such expression vector provides for expression of a fusion protein comprising the sequence encoding TMAH and nucleic acid sequence encoding 6 histidine residues followed by thioredoxin and an enterokinase cleavage site. The histidine residues facilitate purification while the enterokinase cleavage site provides a means for purifying TMAH from the fusion protein.

In addition to recombinant production, fragments of TMAH may be produced by direct peptide synthesis using solid-phase techniques (cf Stewart et al (1969) *Solid-Phase Peptide Synthesis*, WH Freeman Co, San Francisco;

Merrifield J (1963) J Am Chem Soc 85:2149–2154). In vitro protein syntheses may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of TMAH may be chemically synthesized separately and combined using chemical methods to produce the full length molecule.

Uses of TMAH

The rationale for use of the nucleotide and peptide sequences disclosed herein is based on the chemical and structural homology among the novel human macrophage antigen and the A1 (GI 293273; Lin et al. (1993) J Immunol 151:1979–88) and C-type lectin receptor (GI 350597, GI 35059, GI35061; Houchins J P et al (1991) J Exp Med 173:1017–20) gene families. Furthermore, since expression of the A1 family genes is usually associated with cells of hematopoeitic origin, it appears that variants of these genes will be found in similar cells or tissues where they will carry similar functions.

The similarity of TMAH to members of the A1 gene family suggests that enhancing the expression of TMAH would promote cell survival. For example, providing TMAH to joint chondrocytes may result in decreased apoptosis and slow the progressive degeneration associated with the onset of osteoarthritis. Similarly, inducing the expression of TMAH may serve to slow other immune or senescent responses such as the rescue of neurons from programmed cell death due to hypoxia or cerebral ischemic stroke. Thus the expression of TMAH may promote cell survival in cases of immune or senescent diseases including, but are not limited to, AIDS, Alzheimer's disease, arthritis, graft and transplant rejection, lupus erythematosis, and myasthenia gravis.

In those situations where the induction of apoptosis is desirable, cells could be transfected with antisense sequences of the gene encoding TMAH or provided with inhibitors of TMAH. Such diseases include cancers such as lymphoma, malignant melanomas, and carcinomas of the breast, intestine, lung, nasopharynx, and prostate.

TMAH Antibodies

TMAH-specific antibodies are useful for the diagnosis and treatment of conditions and diseases associated with expression of TMAH. Such antibodies include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

TMAH for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of TMAH amino acids may be fused with those of another protein such as keyhole limpet hemocyanin and antibody produced against the chimeric molecule. Procedures well known in the art can be used for the production of antibodies to TMAH.

For the production of antibodies, various hosts including goats, rabbits, rats, mice, etc may be immunized by injection with TMAH or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to TMAH may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy,* Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce TMAH-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for TMAH may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between TMAH and its specific antibody and the measurement of complex formation. A two-site, monoclonal-based immunoassay utilizing monoclonal antibodies reactive to two noninterfering epitopes on a specific TMAH protein is preferred, but a competitive binding assay may also be employed. These assays are described in Maddox D E et al (1983, J Exp Med 158:1211).

Diagnostic Assays Using TMAH Specific Antibodies

Particular TMAH antibodies are useful for the diagnosis of conditions or diseases characterized by expression of TMAH or in assays to monitor patients being treated with TMAH, its fragments, agonists or inhibitors. Diagnostic assays for TMAH include methods utilizing the antibody and a label to detect TMAH in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring TMAH, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on TMAH is preferred, but a competitive binding assay may be employed. These assays are described, among other places, in Maddox, D E et al (1983, J Exp Med 158:1211).

In order to provide a basis for diagnosis, normal or standard values for TMAH expression must be established. This is accomplished by combining body fluids or cell extracts taken from normal subjects, either animal or human, with antibody to TMAH under conditions suitable for complex formation which are well known in the art. The amount of standard complex formation may be quantified by comparing various artificial membranes containing known quantities of TMAH with both control and disease samples from biopsied tissues. Then, standard values obtained from normal samples may be compared with values obtained from samples from subjects potentially affected by disease. Deviation between standard and subject values establishes the presence of disease state.

Drug Screening

TMAH, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between TMAH and the agent being tested, may be measured.

Another technique for drug screening which may be used for high throughput screening of compounds having suitable binding affinity to the TMAH is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of TMAH and washed. Bound TMAH is then detected by methods well known in the art. Substantially purified TMAH can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding TMAH specifically compete with a test compound for binding TMAH. In this manner, the antibodies can be used to detect the presence of any peptide which shares one or more antigenic determinants with TMAH.

Uses of the Polynucleotide Encoding TMAH

A polynucleotide sequence encoding TMAH or any part thereof may be used for diagnostic and/or therapeutic purposes. For diagnostic purposes, the sequence encoding TMAH of this invention may be used to detect and quantitate gene expression in biopsied tissues in which expression of TMAH may be implicated. The diagnostic assay is useful to distinguish between absence, presence, and excess expression of TMAH and to monitor regulation of TMAH levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding TMAH or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring TMAH, alleles or related sequences.

Probes may also be used for the detection of related sequences and should preferably contain at least 50% of the nucleotides from any of these TMAH-encoding sequences. The hybridization probes of the subject invention may be derived from the nucleotide sequence of SEQ ID NO:2 or from genomic sequence including promoter, enhancer elements and introns of the naturally occurring sequence encoding TMAH. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs include the cloning of nucleic acid sequences encoding TMAH or TMAH derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostic Use

Polynucleotide sequences encoding TMAH may be used for the diagnosis of conditions or diseases with which the expression of TMAH is associated. For example, polynucleotide sequences encoding TMAH may be used in hybridization or PCR assays of fluids or tissues from biopsies to detect TMAH expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The TMAH-encoding nucleotide sequences disclosed herein provide the basis for assays-that detect activation or induction associated with inflammation or disease. The nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding TMAH in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for TMAH expression must be established. This is accomplished by combining body fluids or cell extracts taken from normal subjects, either animal or human, with TMAH, or a portion thereof, under conditions suitable for hybridization or amplification. Standard hybridization may be quantified by comparing the values obtained for normal subjects with a dilution series of TMAH run in the same experiment where a known amount of substantially purified TMAH is used. Standard values obtained from normal samples may be compared with values obtained from samples from patients affected by TMAH-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, may be used as described in U.S. Pat. Nos. 4,683, 195 and 4,965,188 provides additional uses for oligonucleotides based upon the sequence encoding TMAH. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to A1 family members and its expression profile, the polynucleotide encoding TMAH disclosed herein may be useful in the treatment of genetic or immune system disorders such as asthma, arthritis, etc and inflammatory conditions.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense of the sequence encoding TMAH. See, for example, the techniques described in Sambrook et al (supra) and Ausubel et al (supra).

The polynucleotides comprising full length cDNA sequence and/or its regulatory elements enable researchers to use the sequence encoding TMAH as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding TMAH can be turned off by transfecting a cell or tissue with expression vectors which express high levels of a desired TMAH fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of the sequence encoding TMAH, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber BE and BI Carr (1994) *Molecular and Immunologic Approaches,* Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of the sequence encoding TMAH.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding TMAH. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences encoding TMAH disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence encoding TMAH can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:149–54).

The technique of fluorescent in situ hybridization of chromosome spreads has been described, among other places, in Verma et al (1988) *Human Chromosomes: A Manual of Basic Techniques,* Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a the sequence encoding TMAH on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T J et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of TMAH, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will-be specific to particular cells, conditions, locations, etc.

It is contemplated, for example, that a therapeutically effective dose of TMAH fragment consisting of amino acid residues $S_{62}$ to $I_{272}$ can be delivered in a suitable formulation to act as a biological sponge against microbes or to deliver another therapeutic molecule to cancerous cells or tissues.

The examples below are provided to illustrate the subject invention and are not included for the purpose of limiting the invention.

EXAMPLES

I cDNA Library Construction

The peripheral blood sample was obtained from a normal 24 year old male Caucasian. Human peripheral blood mononuclear cells were separated from heparinized venous blood after centrifugation through Ficoll/Hypaque. The Ficoll/Hypaque buffy coat which contains peripheral blood mononuclear cells was put into sterile Petri dishes and cultured for between 3 to 5 days in Dulbecco's minimum essential medium (DME) supplemented with 10% human serum.

After the incubation period, macrophages mostly adhered to the plastic surface, whereas most other cell types, B cells and T cells, remained in solution. The DME supplemented with 10% human serum was decanted from the wells and washed with phosphate buffered saline (PBS). Macrophages were released from plastic surface by gently scraping the Petri dishes in PBS/1 mM EDTA. Macrophages were lysed immediately in buffer containing guanidinium isothiocyanate.

Lysates were then loaded on a 5.7 M CsCl cushion and ultracentrifuged in a SW28 swinging bucket rotor for 18 hours at 25,000 rpm at ambient temperature. Total RNA was then ethanol precipitated, washed in 70% ethanol and resuspended in distilled water and DNAse for 15 minutes at 37° C. The RNA was acid phenol extracted and ethanol precipitated. After being washed in 70% ethanol, the polyadenylated RNA was isolated using Oligotex™ resin with spherical latex particles (QIAGEN Inc., Chatsworth Calif.) and quantitated and frozen at −80° C. The isolated poly A+ mRNA was sent to Stratagene (La Jolla, Calif.) for custom cDNA library construction.

Stratagene prepared the cDNA library using oligo d(T) priming where the primer also contains a Not1 site for directional cloning. Synthetic adapter oligonucleotides were ligated onto the cDNA molecules enabling them to be inserted into the Uni-ZAP™ vector system (Stratagene) followed by sizing of the cDNA on a Sephacryl S1000 column. This allowed high efficiency unidirectional (sense orientation) lambda library construction and the convenience of a plasmid system with blue/white color selection to detect clones with cDNA insertions.

The quality of the cDNA library was screened using DNA probes, and then, the pBluescript® phagemid (Stratagene) was excised. This phagemid allows the use of a plasmid system for easy insert characterization, sequencing, site-directed mutagenesis, the creation of unidirectional deletions and expression of fusion polypeptides. Subsequently, the custom-constructed library phage particles were infected into *E. coli* host strain XL1-Blue® (Stratagene). The high transformation efficiency of this bacterial strain increases the probability that the cDNA library contains rare, underrepresented clones. Alternative unidirectional vectors include, but are not limited to, pcDNAI (Invitrogen, San Diego Calif.) and pSHlox-1 (Novagen, Madison Wis.).

The cDNAs were sequenced by the method of Sanger F and AR Coulson (1975; J Mol Biol 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems, and the reading frame was determined.

III Homology Searching of cDNA Clones and Their Deduced Proteins

Each cDNA was compared to sequences in GenBank using a search algorithm developed by Applied Biosystems and incorporated into the INHERIT-670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al. supra).

Analogous computer techniques using BLAST (Altschul S F 1993 and 1990, supra) are used to search for identical or related molecules in nucleotide databases such as GenBank or the LIFESEQ™ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of the Sequence Encoding TMAH

The nucleic acid sequence of SEQ ID NO:2 is used to design oligonucleotide primers for extending a partial nucleotide sequence to full length or for obtaining 5' sequence from genomic libraries. One primer is synthesized to initiate extension in the antisense direction (XLR) and the other is synthesized to extend sequence in the sense direction (XLF). Primers allow the extension of the know sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| Step | Condition |
| --- | --- |
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of $[\gamma\text{-}^{32}P]$ adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I; Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The sequence encoding TMAH, or any part thereof, is used to inhibit in vivo or in vitro expression of naturally occurring sequence. Although use of antisense oligonucleotides, comprising about 20 base-pairs, is specifically described, essentially the same procedure is used with larger cDNA fragments. An oligonucleotide complementary to the coding sequence of TMAH as shown in FIGS. 1A and 1B is used to inhibit expression of naturally occurring sequence. The complementary oligonucleotide is designed from the most unique 5' sequence as shown in FIGS. 1A and 1B and used either to inhibit transcription by preventing promoter binding to the upstream nontranslated sequence or translation of an TMAH-encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A and 1B.

VIII Expression of TMAH

Expression of the TMAH is accomplished by subcloning the cDNAs into appropriate vectors and transfecting the vectors into host cells. In this case, the cloning vector, pSport, previously used for the generation of the cDNA library is used to express TMAH in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length TMAH. The signal sequence directs the secretion of TMAH into the bacterial growth media which can be used directly in the following assay for activity.

IX TMAH Activity

TMAH activity can be assayed in BHK cells seeded on a microscope slide and transiently transfected with the following plasmids: one which contains the nucleic acid sequence encoding TMAH and one which contains tandemly arranged coding sequences for tumor necrosis factor alpha (TNF-α; which causes apoptosis) and B-galactosidase. The cells are fixed after twelve hours and incubated in a buffer containing X-gal to visualize B-galactosidase activity. Phase or interference contrast microscopy is used to examine the slides. Cells expressing only the plasmid with TNF-α display shrunken nuclei, intense blue staining and membrane blebbling. Cells expressing both plasmids show nearly normal nuclei, intense blue staining, and nearly normal membranes, no blebbling. This techniques was adapted from Stanger BZ (1995; Cell 81:513–523.

In the alternative, C-type lectin receptor activity may be assayed by first labeling the polypeptide with $^{125}I$ Bolton-Hunter reagent (Bolton A E and Hunter W M (1973) Biochem J 133: 529). Candidate ligands (including lectins, polysaccharides, glycoproteins) previously arrayed in the wells of a 96 well plate are incubated with membrane fragments containing the labeled TMAH. The plates are washed, assayed and quantitated spectrophotometrically for ligand:TMAH complex. Data obtained using different concentrations of the candidate ligands are used to calculate the number, distribution, and association of TMAH with the candidate ligands.

X Production of TMAH Specific Antibodies

TMAH substantially purified using PAGE electrophoresis (Sambrook, supra) is used to immunize rabbits and to produce antibodies using standard protocols. The amino acid sequence translated from TMAH is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIGS. 4 and 5) is described by Ausubel F M et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant.

The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring TMAH Using Specific Antibodies

Naturally occurring or recombinant TMAH is substantially purified by immunoaffinity chromatography using antibodies specific for TMAH. An immunoaffinity column is constructed by covalently coupling TMAH antibody to an activated chromatographic resin such as CnBr-activated Sepharose (Pharmacia Biotech). After the coupling, the resin is blocked and washed according to the manufacturer's instructions.

Membrane fractions from cells expressing TMAH are prepared by methods well known in the art. Alternatively, a recombinant TMAH fragment containing an appropriate signal sequence may be secreted in useful quantitiy into the medium in which transfected cells are grown.

A TMAH-containing preparation is passed over the immunoaffinity column, and the column is washed under conditions that allow the preferential absorbance of TMAH (eg, high ionic strength buffers in the presence of detergent). The column is eluted under conditions that disrupt antibody/TMAH binding (eg, a buffer of pH 2–3 or a high concentration of a chaotrope such as urea or thiocyanate ion), and TMAH is collected.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A substantially purified polypeptide comprising the amino acid sequence of SEQ ID NO:1.

2. A composition comprising the polypeptide of claim 1 and a pharmaceutically acceptable excipient.

3. A substantially purified fragment of the polypeptide of claim 1 comprising the amino acid sequence of SEQ ID NO:1 from about amino acid residue 62, serine, to amino acid residue 272, isoleucine.

4. A composition comprising the purified fragment of claim 3 and a pharmaceutically acceptable excipient.

5. A purified antibody which binds specifically to the polypeptide of claim 1.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 272 amino acids
      (B) TYPE: amino acid
      (C) STRANDEDNESS: single
      (D) TOPOLOGY: linear (ii) MOLECULE TYPE: peptide (vii) IMMEDIATE SOURCE:
      (A) LIBRARY: MPHGNOT03
      (B) CLONE: 513418

(xi) SEQUENCE DESCRIPTION: SEQ ID NO:1:

```
Met Ser Glu Glu Val Thr Tyr Ala Asp Leu Gln Phe Gln Asn Ser Ser
 1               5                  10                  15

Glu Met Glu Lys Ile Pro Glu Ile Gly Lys Phe Gly Glu Lys Ala Pro
                20                  25                  30

Pro Ala Pro Ser His Val Trp Arg Pro Ala Ala Leu Phe Leu Thr Leu
                35                  40                  45

Leu Cys Leu Leu Leu Leu Ile Gly Leu Gly Val Leu Ala Ser Met Phe
    50                  55                  60

His Val Thr Leu Lys Ile Glu Met Lys Lys Met Asn Lys Leu Gln Asn
65                  70                  75                  80

Ile Ser Glu Glu Leu Gln Arg Asn Ile Ser Leu Gln Leu Met Ser Asn
                85                  90                  95

Met Asn Ile Ser Asn Lys Ile Arg Asn Leu Ser Thr Thr Leu Gln Thr
                100                 105                 110

Ile Ala Thr Lys Leu Cys Arg Glu Leu Tyr Ser Lys Glu Gln Glu His
            115                 120                 125

Lys Cys Lys Pro Cys Pro Arg Arg Trp Ile Trp His Lys Asp Ser Cys
        130                 135                 140

Tyr Phe Leu Ser Asp Asp Val Gln Thr Trp Gln Glu Ser Lys Met Ala
```

|   |   |   | 145 |   |   |   | 150 |   |   |   | 155 |   |   |   | 160 |
|---|---|---|---|---|---|---|---|---|---|---|---|---|---|---|---|
Cys Ala Ala Gln Asn Ala Ser Leu Leu Lys Ile Asn Asn Lys Asn Ala
               165                 170                 175

Leu Glu Phe Ile Lys Ser Gln Ser Arg Ser Tyr Asp Tyr Trp Leu Gly
            180                 185                 190

Leu Ser Pro Glu Glu Asp Ser Thr Arg Gly Met Arg Val Asp Asn Ile
        195                 200                 205

Ile Asn Ser Ser Ala Trp Val Ile Arg Asn Ala Pro Asp Leu Asn Asn
        210                 215                 220

Met Tyr Cys Gly Tyr Ile Asn Arg Leu Tyr Val Gln Tyr Tyr His Cys
225                 230                 235                 240

Thr Tyr Lys Lys Arg Met Ile Cys Glu Lys Met Ala Asn Pro Val Gln
            245                 250                 255

Leu Val Leu His Ile Leu Gly Arg His Glu Ala Ser Ile Lys Tyr Ile
            260                 265                 270

(2) INFORMATION FOR SEQ ID NO:2:

(i) SEQUENCE CHARACTERISTICS:
        (A) LENGTH: 970 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: MPHGNOT03
        (B) CLONE: 513418

(xi) SEQUENCE DESCRIPTION: SEQ ID NO:2:

GAAGTGTAAA CTTGTAAGCT TAAGCTTCCG TTTATAAACA GAAGTTTAAA ATTATAGGTC      60

CTGTTTAACA TTCAGCTCTG TTAACTCACT CATCTTTTTG TGTTTTTACA CTTTGTCAAG     120

ATTTCTTTAC ATATTCATCA ATGTCTGAAG AAGTTACTTA TGCAGATCTT CAATTCCAGA     180

ACTCCAGTGA GATGGAAAAA ATCCCAGAAA TTGGCAAATT TGGGGAAAAA GCACCTCCAG     240

CTCCCTCTCA TGTATGGCGT CCAGCAGCCT TGTTTCTGAC TCTTCTGTGC CTTCTGTTGC     300

TCATTGGATT GGGAGTCTTG GCAAGCATGT TCATGTAAC TTTGAAGATA GAAATGAAAA      360

AAATGAACAA ACTACAAAAC ATCAGTGAAG AGCTCCAGAG AAATATTTCT CTACAACTGA     420

TGAGTAACAT GAATATCTCC AACAAGATCA GGAACCTCTC CACCACACTG CAAACAATAG     480

CCACCAAATT ATGTCGTGAG CTATATAGCA AGAACAAGA GCACAAATGT AAGCCTTGTC      540

CAAGGAGATG GATTTGGCAT AAGGACAGCT GTTATTTCCT AAGTGATGAT GTCCAAACAT     600

GGCAGGAGAG TAAAATGGCC TGTGCTGCTC AGAATGCCAG CCTGTTGAAG ATAAACAACA     660

AAAATGCATT GGAATTTATA AAATCCCAGA GTAGATCATA TGACTATTGG CTGGGATTAT     720

CTCCTGAAGA AGATTCCACT CGTGGTATGA GAGTGGATAA TATAATCAAC TCCTCTGCCT     780

GGGTTATAAG AAACGCACCT GACTTAAATA ACATGTATTG TGGATATATA AATAGACTAT     840

ATGTTCAATA TTATCACTGC ACTTATAAAA AAAGAATGAT ATGTGAGAAG ATGGCCAATC     900

CAGTGCAGTT GGTTCTACAT ATTTTAGGGA GGCATGAGGC ATCAATCAAA TACATTTAAG     960

GAGTGTAGGG                                                           970

(2) INFORMATION FOR SEQ ID NO:3:

(i) SEQUENCE CHARACTERISTICS:
        (A) LENGTH: 172 amino acids

```
            (B) TYPE: amino acid
            (C) STRANDEDNESS: single
            (D) TOPOLOGY: linear (ii) MOLECULE TYPE: peptide (vii) IMMEDIATE SOURCE:
            (A) LIBRARY: GenBank
            (B) CLONE: 293274

(xi) SEQUENCE DESCRIPTION: SEQ ID NO:3:

Met Ala Glu Ser Glu Leu Met His Ile His Ser Leu Ala Glu His Tyr
 1               5                  10                  15

Leu Gln Tyr Val Leu Gln Val Pro Ala Phe Glu Ser Ala Pro Ser Gln
                20                  25                  30

Ala Cys Arg Val Leu Gln Arg Val Ala Phe Ser Val Gln Lys Glu Val
            35                  40                  45

Glu Lys Asn Leu Lys Ser Tyr Leu Asp Asp Phe His Val Glu Ser Ile
         50                  55                  60

Asp Thr Ala Arg Ile Ile Phe Asn Gln Val Met Glu Lys Glu Phe Glu
65                  70                  75                  80

Asp Gly Ile Ile Asn Trp Gly Arg Ile Val Thr Ile Phe Ala Phe Gly
                85                  90                  95

Gly Val Leu Leu Lys Lys Leu Pro Gln Glu Gln Ile Ala Leu Asp Val
               100                 105                 110

Cys Ala Tyr Lys Gln Val Ser Ser Phe Val Ala Glu Phe Ile Met Asn
           115                 120                 125

Asn Thr Gly Glu Trp Ile Arg Gln Asn Gly Gly Trp Glu Asp Gly Phe
       130                 135                 140

Ile Lys Lys Phe Glu Pro Lys Ser Gly Trp Leu Thr Phe Leu Gln Met
145                 150                 155                 160

Thr Gly Gln Ile Trp Glu Met Leu Phe Leu Leu Lys
               165                 170

(2) INFORMATION FOR SEQ ID NO:4:

(i) SEQUENCE CHARACTERISTICS:
            (A) LENGTH: 239 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (A) LIBRARY: GenBank
            (B) CLONE: 179367

(xi) SEQUENCE DESCRIPTION: SEQ ID NO:4:

Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
                20                  25                  30

Gly Asp Val Gly Ala Ala Pro Pro Gly Ala Ala Pro Ala Pro Gly Ile
            35                  40                  45

Phe Ser Ser Gln Pro Gly His Thr Pro His Pro Ala Ala Ser Arg Asp
         50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Ala
                85                  90                  95
```

-continued

```
Leu Arg Gln Ala Gly Asp Asp Phe Ser Arg Arg Tyr Arg Gly Asp Phe
            100                 105                 110
Ala Glu Met Ser Ser Gln Leu His Leu Thr Pro Phe Thr Ala Arg Gly
            115                 120                 125
Arg Phe Ala Thr Val Val Glu Glu Leu Phe Arg Asp Gly Val Asn Trp
            130                 135                 140
Gly Arg Ile Val Ala Phe Phe Glu Phe Gly Gly Val Met Cys Val Glu
145                 150                 155                 160
Ser Val Asn Arg Glu Met Ser Pro Leu Val Asp Asn Ile Ala Leu Trp
                165                 170                 175
Met Thr Glu Tyr Leu Asn Arg His Leu His Thr Trp Ile Gln Asp Asn
            180                 185                 190
Gly Gly Trp Asp Ala Phe Val Glu Leu Tyr Gly Pro Ser Met Arg Pro
            195                 200                 205
Leu Phe Asp Phe Ser Trp Leu Ser Leu Lys Thr Leu Leu Ser Leu Ala
            210                 215                 220
Leu Val Gly Ala Cys Ile Thr Leu Gly Ala Tyr Leu Ser His Lys
225                 230                 235
```

(2) INFORMATION FOR SEQ ID NO:5:

(i) SEQUENCE CHARACTERISTICS:
        (A) LENGTH: 197 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 34678

(xi) SEQUENCE DESCRIPTION: SEQ ID NO:5:

```
Met Ala Pro Lys Lys Pro Glu Pro Lys Lys Glu Ala Ala Lys Pro Met
1               5                   10                  15
Asn Val Lys Met Leu Asp Phe Glu Thr Phe Leu Pro Ile Leu Ala Pro
            20                  25                  30
Ala Pro Ala Pro Ala Pro Ala Pro Ala Pro Ala Pro Gln His Ile
            35                  40                  45
Ser Arg Asn Lys Glu Gln Gly Thr Tyr Glu Asp Phe Pro Glu Ala Pro
            50                  55                  60
Lys Glu Pro Ala Phe Asp Pro Lys Ser Val Lys Val Glu Gly Leu Arg
65                  70                  75                  80
Val Phe Asp Lys Glu Ser Asn Gly Thr Val Ile Asp Phe Thr Ala Asp
                85                  90                  95
Gln Ile Glu Glu Phe Lys Glu Ala Phe Met Gly Ala Glu Leu Arg His
            100                 105                 110
Val Leu Ala Thr Leu Gly Glu Lys Ser Leu Phe Asp Arg Thr Pro Thr
            115                 120                 125
Gly Glu Met Lys Ile Thr Tyr Met Thr Glu Ala Glu Val Glu Gln Leu
            130                 135                 140
Leu Ala Gly Gln Glu Asp Gly Gln Cys Gly Asp Val Leu Arg Ala Leu
145                 150                 155                 160
Gly Gln Asn Pro Thr Ala Asn Gly Cys Ile Asn Tyr Glu Ala Phe Val
                165                 170                 175
Lys His Ile Met Asn Ala Glu Val Leu Arg Val Leu Gly Lys Pro Lys
```

```
                    180               185               190
Pro Glu Glu Ser Gly
            195

(2) INFORMATION FOR SEQ ID NO:6:

(i) SEQUENCE CHARACTERISTICS:
        (A) LENGTH: 231 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 35061

(xi) SEQUENCE DESCRIPTION: SEQ ID NO:6:

Met Ser Lys Gln Arg Gly Thr Phe Ser Glu Val Ser Leu Ala Gln Asp
 1               5                  10                  15

Pro Lys Arg Gln Gln Arg Lys Pro Lys Gly Asn Lys Ser Ser Ile Ser
            20                  25                  30

Gly Thr Glu Gln Glu Ile Phe Gln Val Glu Leu Asn Leu Gln Asn Pro
        35                  40                  45

Ser Leu Asn His Gln Gly Ile Asp Lys Ile Tyr Asp Cys Gln Gly Leu
    50                  55                  60

Leu Pro Pro Pro Glu Lys Leu Thr Ala Glu Val Leu Gly Ile Ile Cys
65                  70                  75                  80

Ile Val Leu Met Ala Thr Val Leu Lys Thr Ile Val Leu Ile Pro Phe
                85                  90                  95

Leu Glu Gln Asn Asn Ser Ser Pro Asn Thr Arg Thr Gln Lys Ala Arg
            100                 105                 110

His Cys Gly His Cys Pro Glu Glu Trp Ile Thr Tyr Ser Asn Ser Cys
        115                 120                 125

Tyr Tyr Ile Gly Lys Glu Arg Arg Thr Trp Glu Glu Ser Leu Leu Ala
    130                 135                 140

Cys Thr Ser Lys Asn Ser Ser Leu Leu Ser Ile Asp Asn Glu Glu Glu
145                 150                 155                 160

Ile Lys Phe Leu Ala Ser Ile Leu Pro Ser Ser Trp Ile Gly Val Phe
                165                 170                 175

Arg Asn Ser Ser His His Pro Trp Val Thr Ile Asn Gly Leu Ala Phe
            180                 185                 190

Lys His Lys Ile Lys Asp Ser Asp Asn Ala Glu Leu Asn Cys Ala Val
        195                 200                 205

Leu Gln Val Asn Arg Leu Lys Ser Ala Gln Cys Gly Ser Ser Met Ile
    210                 215                 220

Tyr His Cys Lys His Lys Leu
225                 230

(2) INFORMATION FOR SEQ ID NO:7:

(i) SEQUENCE CHARACTERISTICS:
        (A) LENGTH: 215 amino acids
        (B) TYPE: amino acid
        (C) STRANDEDNESS: single
        (D) TOPOLOGY: linear (ii) MOLECULE TYPE: peptide (vii) IMMEDIATE SOURCE:
```

```
          (A) LIBRARY: GenBank
          (B) CLONE: 35059

(xi) SEQUENCE DESCRIPTION: SEQ ID NO:7:

Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
                20                  25                  30

Ala Thr Glu Gln Glu Ile Thr Tyr Ala Glu Leu Asn Leu Gln Lys Ala
            35                  40                  45

Ser Gln Asp Phe Gln Gly Asn Asp Lys Thr Tyr His Cys Lys Asp Leu
50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Arg
                85                  90                  95

His Cys Gly His Cys Pro Glu Glu Trp Ile Thr Tyr Ser Asn Ser Cys
                100                 105                 110

Tyr Tyr Ile Gly Lys Glu Arg Arg Thr Trp Glu Glu Ser Leu Leu Ala
            115                 120                 125

Cys Thr Ser Lys Asn Ser Ser Leu Leu Ser Ile Asp Asn Glu Glu Glu
130                 135                 140

Met Lys Phe Leu Ser Ile Ile Ser Pro Ser Ser Trp Ile Gly Val Phe
145                 150                 155                 160

Arg Asn Ser Ser His His Pro Trp Val Thr Met Asn Gly Leu Ala Phe
                165                 170                 175

Lys His Glu Ile Lys Asp Ser Asp Asn Ala Glu Leu Asn Cys Ala Val
            180                 185                 190

Leu Gln Val Asn Arg Leu Lys Ser Ala Gln Cys Gly Ser Ser Ile Ile
            195                 200                 205

Tyr His Cys Lys His Lys Leu
210                 215

(2) INFORMATION FOR SEQ ID NO:8:

(i) SEQUENCE CHARACTERISTICS:
          (A) LENGTH: 233 amino acids
          (B) TYPE: amino acid
          (C) STRANDEDNESS: single
          (D) TOPOLOGY: linear (ii) MOLECULE TYPE: peptide (vii) IMMEDIATE SOURCE:
          (A) LIBRARY: GenBank
          (B) CLONE: 35057

(xi) SEQUENCE DESCRIPTION: SEQ ID NO:8:

Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
                20                  25                  30

Ala Thr Glu Gln Glu Ile Thr Tyr Ala Glu Leu Asn Leu Gln Lys Ala
            35                  40                  45

Ser Gln Asp Phe Gln Gly Asn Asp Lys Thr Tyr His Cys Lys Asp Leu
50                  55                  60

Pro Ser Ala Pro Glu Lys Leu Ile Val Gly Ile Leu Gly Ile Ile Cys
65                  70                  75                  80
```

-continued

```
Leu Ile Leu Met Ala Ser Val Val Thr Ile Val Val Ile Pro Ser Thr
                 85                  90                  95

Leu Ile Gln Arg His Asn Asn Ser Ser Leu Asn Thr Arg Thr Gln Lys
                100                 105                 110

Ala Arg His Cys Gly His Cys Pro Glu Glu Trp Ile Thr Tyr Ser Asn
                115                 120                 125

Ser Cys Tyr Tyr Ile Gly Lys Glu Arg Thr Trp Glu Ser Leu
130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ile Ser Pro Ser Ser Trp Ile Gly
                165                 170                 175

Val Phe Arg Asn Ser Ser His His Pro Trp Val Thr Met Asn Gly Leu
                180                 185                 190

Ala Phe Lys His Glu Ile Lys Asp Ser Asp Asn Ala Glu Leu Asn Cys
                195                 200                 205

Ala Val Leu Gln Val Asn Arg Leu Lys Ser Ala Gln Cys Gly Ser Ser
                210                 215                 220

Ile Ile Tyr His Cys Lys His Lys Leu
225                 230
```

(2) INFORMATION FOR SEQ ID NO:9:

(i) SEQUENCE CHARACTERISTICS:
        (A) LENGTH: 179 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1098617

(xi) SEQUENCE DESCRIPTION: SEQ ID NO:9:

```
Met Ala Val Phe Lys Thr Thr Leu Trp Arg Leu Ile Ser Gly Thr Leu
1               5                   10                  15

Gly Ile Ile Cys Leu Ser Leu Met Ala Thr Leu Gly Ile Leu Leu Lys
                20                  25                  30

Asn Ser Phe Thr Lys Leu Ser Ile Glu Pro Ala Phe Thr Pro Gly Pro
                35                  40                  45

Asn Ile Glu Leu Gln Lys Asp Ser Asp Cys Cys Ser Cys Gln Glu Lys
50                  55                  60

Trp Val Gly Tyr Arg Cys Asn Cys Tyr Phe Ile Ser Ser Glu Gln Lys
65                  70                  75                  80

Thr Trp Asn Glu Ser Arg His Leu Cys Ala Ser Gln Lys Ser Ser Leu
                85                  90                  95

Leu Gln Leu Gln Asn Thr Asp Glu Leu Asp Phe Met Ser Ser Ser Gln
                100                 105                 110

Gln Phe Tyr Trp Ile Gly Leu Ser Tyr Ser Glu Glu His Thr Ala Trp
                115                 120                 125

Leu Trp Glu Asn Gly Ser Ala Leu Ser Gln Tyr Leu Phe Pro Ser Phe
                130                 135                 140

Glu Thr Phe Asn Thr Lys Asn Cys Ile Ala Tyr Asn Pro Asn Gly Asn
145                 150                 155                 160
```

```
Ala Leu Asp Glu Ser Cys Glu Asp Lys Asn Arg Tyr Ile Cys Lys Gln
            165                 170                 175
Gln Leu Ile
```